United States Patent
Nihlstrand et al.

(10) Patent No.: US 7,396,783 B2
(45) Date of Patent: Jul. 8, 2008

(54) FIBROUS STRUCTURE AND ABSORBENT ARTICLE COMPRISING SAID FIBROUS STRUCTURE

(75) Inventors: Anna Nihlstrand, Molndal (SE); Barbro Moberg-Alehammar, Molndal (SE); Shabira Abbas, Gothenburg (SE); Asa Lindstrom, Gothenburg (SE); Alain Villermet, Viroflay (FR); Francois Coeuret, Guyancourt (FR); Panayotis Cocolios, Bullion (FR); Bernd Martens, Hamburg (DE); Eckhard Prinz, Hamburg (DE); Franck Forster, Hamburg (DE)

(73) Assignee: SCA Hygiene Products AB, Gothenburg (SE)

( * ) Notice: Subject to any disclaimer, the term of this patent is extended or adjusted under 35 U.S.C. 154(b) by 455 days.

(21) Appl. No.: 10/203,008

(22) PCT Filed: Feb. 2, 2001

(86) PCT No.: PCT/SE01/00203

§ 371 (c)(1),
(2), (4) Date: Nov. 26, 2002

(87) PCT Pub. No.: WO01/57306

PCT Pub. Date: Aug. 9, 2001

(65) Prior Publication Data

US 2003/0153227 A1    Aug. 14, 2003

(30) Foreign Application Priority Data

Feb. 4, 2000 (EP) .................................. 00850022
Feb. 4, 2000 (SE) .................................... 0000367

(51) Int. Cl.
    B32B 27/04 (2006.01)
    C11D 3/00 (2006.01)
    C23C 16/00 (2006.01)

(52) U.S. Cl. ................. 442/118; 8/115.51; 427/255.15; 427/255.18

(58) Field of Classification Search ................. 442/118; 8/115.51
    See application file for complete search history.

(56) References Cited

U.S. PATENT DOCUMENTS 5,474,839 A * 12/1995 Ogawa et al. ................. 442/80

(Continued)

FOREIGN PATENT DOCUMENTS

EP    0 372 890    6/1990

(Continued)

OTHER PUBLICATIONS

Kamath et al. "Effect of surfactant additives on polypropylene nonwovens," 1998 Nonwovens Conference & Trade Fair, pp. 87-93. XP-002142851 (Abstract only).

*Primary Examiner*—Lynda Salvatore
(74) *Attorney, Agent, or Firm*—Young & Thompson

(57) ABSTRACT

A fibrous structure testable in a series of run-off tests, wherein each run-off test includes exposing the fibrous structure to a volume of a test solution and the fibrous structure initially is hydrophobic and has been treated to be hydrophilic, wherein the fibrous structure exhibits a run-off level that is less than 5 percent by weight throughout a series of run-off tests, and wherein the series starts with a first run-off test and ends with a fifth run-off test.

22 Claims, 2 Drawing Sheets

U.S. PATENT DOCUMENTS

Figure 1:
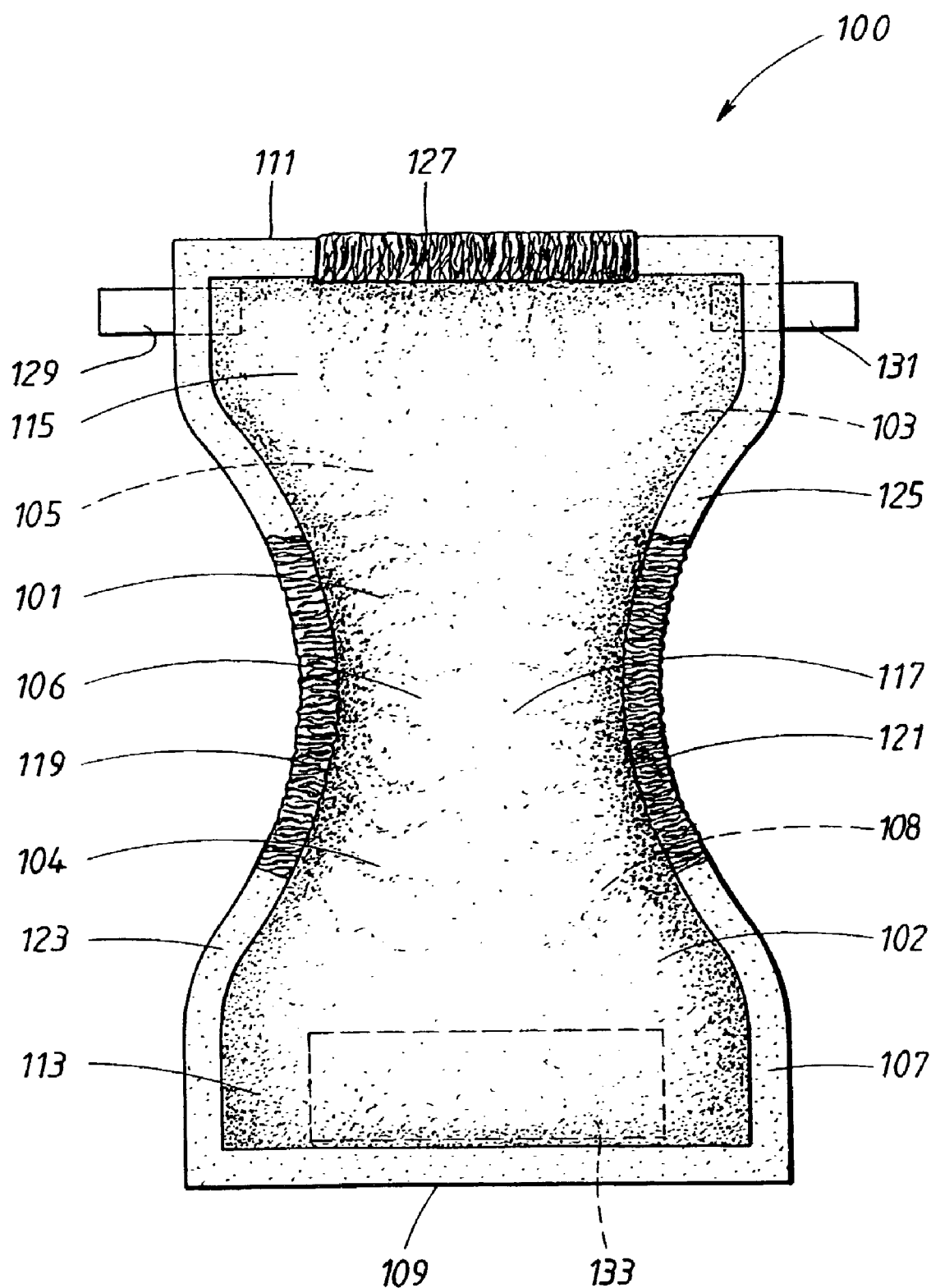

| | | |
|---|---|---|
| 5,523,124 A | 6/1996 | Slootman et al. |
| 5,527,629 A | 6/1996 | Gastiger et al. |
| 5,576,076 A | 11/1996 | Slootman et al. |
| 5,629,088 A | 5/1997 | Ogawa et al. |
| 5,693,037 A | 12/1997 | Lee et al. |
| 5,814,567 A | 9/1998 | Yahiaoui et al. |
| 6,261,679 B1 * | 7/2001 | Chen et al. ............... 428/317.9 |

FOREIGN PATENT DOCUMENTS

| | | |
|---|---|---|
| EP | 0 483 859 | 5/1992 |
| EP | 0 524 529 | 1/1993 |
| WO | 98/10726 | 3/1998 |
| WO | 99 05358 | 2/1999 |
| WO | 00 08248 | 2/2000 |
| WO | 00 16913 | 3/2000 |

* cited by examiner

FIBROUS STRUCTURE AND ABSORBENT ARTICLE COMPRISING SAID FIBROUS STRUCTURE

TECHNICAL FIELD

The present invention provides a fibrous structure which exhibits excellent properties of "hydrophilicity" or "wettability", wherein the properties of "hydrophilicity" or "wettability" are both immediate and durable.

Further, the present invention relates to a fibrous structure (either of a woven or a non-woven type, and of a natural or synthetic material), being testable in a series of run-off tests, wherein each run-off test comprises exposing said fibrous structure to a volume of a test solution and said fibrous structure initially is hydrophobic and has been treated to be hydrophilic.

Moreover, the present invention relates to a fibrous structure having one or more types of polar, silicon-containing compounds bonded to at least one portion of the surface of said fibrous structure.

The present invention also provides an absorbent article comprising an absorption body and at least one of said fibrous structure, wherein said at least one fibrous structure exhibits excellent properties of "hydrophilicity" or "wettability", wherein the properties of "hydrophilicity" or "wettability" are both immediate and durable.

Further, the present invention relates to an absorbent article comprising an absorption body and at least one of said fibrous structure, said at least one fibrous structure may be tested in a series of run-off tests, wherein each run-off test comprises exposing said at least one fibrous structure to a volume of a test solution and said at least one fibrous structure initially is hydrophobic and has been treated to be hydrophilic.

Furthermore, the present invention relates to an absorbent article comprising an absorption body and at least one of said fibrous structure, said at least one fibrous structure is initially hydrophobic and has been treated to be hydrophilic, wherein the absorbent article may be tested in a series of run-off tests and each run-off test comprises exposing said absorbent article to a volume of a test solution.

Still further, the present invention relates to an absorbent article comprising an absorption body and at least one of said fibrous structure, wherein said at least one fibrous structure has one or more types of polar, silicon-containing compounds bonded to at least one portion of the surface of said at least one fibrous structure.

In accordance with the fibrous structure and the absorbent article of the invention, properties of hydrophilicity will be particularly looked for.

Taking the example of an absorbent article comprising fibrous structures made of non-woven materials, the fibrous structures are produced from comparatively hydrophobic synthetic fibres such as, for example, fibres of polypropylene or polyethylene which are treated in order to make the materials liquid permeable.

Further, the present invention also relates to use of said fibrous structure, tissue product and nonvowen material made of said fibrous structure, and to use of said absorbent article.

BACKGROUND ART

In order to obtain fluid absorbent articles which exhibit good wicking ability, a high total and local fluid uptake capacity, good fluid retaining capacity and a high degree of surface dryness, such articles are usually built up of a plurality of different fibrous structures having different functions. The fibrous structures are often produced of inherently hydrophobic materials, e.g. nonwoven materials, and thus such inherently hydrophobic fibrous structures need to be modified to allow fluid uptake. One major problem when constructing fluid absorbent articles of this kind is, however, that it is difficult to obtain optimal wettability, i.e. an optimal degree of hydrophilicity, which is both immediate and durable, i.e. remains unchanged after the article has been exposed to wetting. Furthermore, it is difficult to maintain stable wetting characteristics in absorbent articles, which are stored for an extended period of time.

Regarding fluid permeable cover sheets, which are suitable made of said fibrous structures, for use in absorbent articles such as diapers, incontinence guards and sanitary napkins, wherein the cover sheet is intended to be in contact with the body of a user during use, it is important that the cover sheet immediately exhibits a desired wettability and could stand repeated wettings. In other words, the cover sheet should immediately exhibit an optimal degree of hydrophilicity and remain fluid permeable even after the absorbent article has been exposed to fluid impact several times. Furthermore, it is important that the cover sheet can accept a large amount of fluid during a short interval of time. Another important property of the fluid permeable cover sheet is the ability to exhibit high surface dryness even after having been exposed to several wettings. In order to obtain a cover sheet having the desired properties, it is important that the cover sheet immediately exhibits an optimal, i.e. a desired, degree of hydrophilicity and that the degree of hydrophilicity varies only within a very limited range when the fibrous structure is wetted or when it is subjected to ageing.

As well known to the man skilled in the art, the literature of these fields talk about the properties of "hydrophilicity" or "wettability" of a substrate and often report measurements of "run-off" and "surface tension" to evaluate such properties.

Commonly used methods for increasing the wettability of fluid permeable fibrous structure or of fluid permeable cover sheets both for use as cover sheets in absorbent articles (the same applies to any fibrous structure to be used in absorbent articles) are:

Treatment of the fibrous structure or of the material of said cover sheets with surface active agents, wherein an increased amount of surface active agents has been used to further increase said wettability. Further, treatment with surface active agents here includes use of mixtures of surfactants, e.g. a mixture of a co-wetting agent (reducing surface tension of the fluid which leads to a rapid inlet) and a surfactant having a more durable character, or addition of surface active agents as internal additives.

Exposure of the material of said fibrous structure, or of the material of said cover sheets, to a corona treatment in combination with any addition of hydrophilic substances, methods for corona treatment are for example described in U.S. Pat. No. 5,576,076, U.S. Pat. No. 5,527,629 and U.S. Pat. No. 5,523,124.

The treatment of the fibrous structures or the cover sheets with surface active agents is for example carried out by coating the hydrophobic material with a surface active agent. In order for a material to be fluid permeable the contact angle between the surface of the material and the fluid must be less than 90°. However, a problem in connection with using fibrous structure or cover sheets which have been coated with a surface active agent is that such fibrous structures or cover sheets exhibit decreasing fluid permeability with repeated wetting. The reason for this is that the applied surface active agents are not firmly attached to the surface of the cover material and will be detached from the cover material and solved in body fluid during the first wetting. At subsequent wetting the amount of surface active agent which remains on the surface of the cover sheet is considerably reduced, resulting in impaired fluid permeability. The same applies to absorbent articles when said surface active agents are added as internal additives, because surface active agents added as internal additives do not migrate fast enough to the surface of the absorbent article after wettings of said surface.

Further problems with the treatment of the fibrous structure, or the cover sheets, with surface active agents, besides the lacking durability, are problems which also increases with increased amount of added surface active agent, for example skin irritation which is caused by migration of surface active agents from the cover sheet to the skin of the user, and influence of the absorbent core comprised in said absorbent articles also because of said migration of surface active agents.

Further, commonly used air corona treatment (optionally in combination with addition of hydrophilic substances) does not render any absorbent articles exhibiting an optimal, i.e. a desired, degree of hydrophilicity which is durable. Said degree of hydrophilicity is not durable since said commonly used corona treatment may create a low molecular weight material which is not properly bonded to the surface. Hence subsequent wetting of the surface of the cover sheet may partly remove the created low molecular weight material and added hydrophilic substances and thus resulting in impaired fluid permeability.

In U.S. Pat. No. 5,814,567 a durable hydrophilic coating for a porous hydrophobic substrate is desribed, which may include exposing the substrate to a field of reactive species.

Moreover at a first wetting by a fluid, in U.S. Pat. No. 5,814,567 said hydrophilic coating does not decrease the surface tension of said fluid.

European patent application 98402010.7 (not published) describes fibrous structures which exhibits a well defined rate of wetting and may be useful in absorbent articles. The fibrous structures of the European patent application 98402010.7 have one or more types of polar, silicon-containing compounds bonded to their surfaces but said fibrous structures are not treated with any surface active agent, i.e. no surface active agent at all is added. Thus absorbent articles comprising the fibrous structures described in European patent application 98402010.7 do not show any of the above described problems related to conventional surface active agent treatment or to commonly used corona treatment (optionally in combination with addition of hydrophilic substances).

Nevertheless there is still a need for further modifications of fibrous structures comprised in absorbent articles not showing any of or at least significantly reducing the problems related to conventional surface active agent treatment or to commonly used corona treatment (optionally in combination with addition of hydrophilic substances), especially there is a need for such absorbent articles exhibiting excellent properties of "hydrophilicity" or "wettability" which are both immediate and durable.

DISCLOSURE OF THE INVENTION

The present invention provides a fibrous structures which exhibiting excellent properties of "hydrophilicity" or "wettability", wherein the properties of "hydrophilicity" or "wettability" are both immediate and durable. A fibrous structure, or any material structure, acts hydrophobic when a contact angle between said structure and water is greater than 90° and/or when a contact angle between individual fibres of said structure and water is greater than 90°.

The present invention relates to a fibrous structure, which may be tested in series of run-off tests, wherein each run-off test comprises exposing said fibrous structure to a volume of a test solution, wherein the test solution may be, for example, test solution 1 which will be described later. Moreover, said fibrous structure is initially hydrophobic and has been treated to be hydrophilic. Furthermore, said fibrous structure exhibits a run-off level that is less than five percent by weight throughout a series of run-off tests wherein the series starts with a first run-off test and ends with a fifth run-off test. Said volume may be e.g. 25 ml and the test solution may after the first run-off test have a surface tension which is less than $60*10^{-3}$ N/m.

Further, said fibrous structures may consist of one or more non-woven materials. Moreover, the fibrous structures may for instance be used as fluid permeable cover sheet for absorbent articles or as a fluid transfer layer between the fluid permeable cover sheet and an absorbent structure (the absorption body) in an absorbent article, or for the absorbent structure itself. Further, said one or more fibrous structures may constitute a part or all of the fluid pervious cover layer and/or of a fluid transfer layer positioned between the fluid pervious cover layer and the absorption body. Still further, the fibrous structures may comprise one or more tissue layers.

Further the fibrous structure may be used for tissue products. As well known to the man skilled in the art, the term "tissue" commonly covers fibrous material based on cellulose or cellulose in combination with synthetic fibres. Tissue are typically used in the manufacture of household items such as kitchen towels, toilet paper, napkins or wipes, in the manufacture of layers entering the structure of absorbent articles such as diapers, incontinence guards, sanitary napkins, or the like.

However, said fibrous structure is initially hydrophobic and has been treated to be hydrophilic.

Further, a fibrous structure according to the invention is initially hydrophobic and has been treated to be hydrophilic and exhibits a run-off level that is less than two percent by weight throughout the series of run-off tests, as defined herein, wherein the series starts with a first run-off test and ends with a fifth run-off test.

A further embodiment according to the present invention discloses a fibrous structure, wherein said volume is 25 ml and said test solution after the first run-off test has a surface tension which is less than $60*10^{-3}$ N/m.

Still further, a fibrous structure according to the invention as described herein exhibits a run-off level that is zero throughout the series of run-off tests, as defined herein, wherein the series starts with a first run-off test and ends with a fifth run-off test.

Furthermore, a fibrous structure article according to the invention as described herein exhibits the afore-mentioned run-off level throughout said series of run-off tests, wherein said run-off level has been accomplished by bonding one or more types of polar, silicon-containing compounds, to at least one portion of the surface of the fibrous structure.

Even further, a fibrous structure article according to the invention as described herein exhibits the afore-mentioned run-off level throughout said series of run-off tests, wherein said run-off level has been accomplished by bonding one or more types of polar, silicon-containing compounds, to at least one portion of the surface of the fibrous structure and then adding a surface active agent or a composition comprising a surface active agent. Further, an alternative to accomplish said run-off level may be to by adding to the fibrous structure a surface active agent or a composition comprising a surface active agent, and then bonding one or more types of polar, silicon-containing compounds, to at least one portion of the surface of the fibrous structure.

In general, materials with added surface active agents act hydrophilic or decrease the surface tension of the liquid in contact with said material. Moreover, detergents, wetting agents (surfactants) and emulsifiers are the three general categories of surface active agents.

The surface active agent as used herein may be composed of one surface active agent or may be any suitable mixture of two or more surface active agents. Further, the surface active agent may be, for example, any suitable anionic, cationic, nonionic or zwitterionic surface active agents, i.e. salts of quaternary amines or fatty acids, sulphates, sulphonates, amines or derivatives thereof, polymeric surfactants, or any suitable amphiphilic proteins.

In anionic, cationic, zwitterionic and nonionic surface active agents the hydrophobic part may be a hydrocarbon chain, a polyoxypropylene chain, perfluoroalkyl or polysiloxane; the anionic part may be carboxylic acid salts, sulphonic acid salts, sulphuric acid ester salts, phosphoric or polyphosphoric esters, or perfluorinated anions; the cationic part may be long-chain amines, diamines, polyamines, or any suitable salts thereof, quaternary ammonium salts, polyoxyethylenated (POE) long-chain amines, quaternized polyoxyethylenated (POE) long-chain amines, or amine oxides; the non-ionic part may be polyoxyethylenated alkylphenols, alkylphenol "ethoxylates" (APE), polyoxyethylenated straight chain alcohols, alcohol "ethoxylates" (AE) polyoxyethylenated polyoxypropylene glycols, polyoxyethylenated mercaptans, long chain carboxylic acid esters, alkanolamine "condensates" alkanolamides, polyoxyethylenated silicones, n-alkylpyrrolidones or alkyl polyglycosides; and the zwitterionic part may be pH-sensitive, i.e. β-n-alkylaminopropionic acids, n-alkyl-β-iminodipropionic acids, imidozoline carboxylates, n-alkylbetaines or amine oxides, or pH-insensitive, e.g. sulfobetaines.

A composition comprising a surface active agent may be for example a lotion; a hydrophilic glue, a hydrophilic skin care product; and/or similar.

The hydrophilic glue which is used to achieve the desired properties of said fibrous structures may be e.g. a dispersion glue or a modified hydrophobic glue (i.e. a melting glue) which is modified to be hydrophilic.

Further, when the surface active agent or the composition comprising the surface active agent is added as an internal additive to the fibrous structure prior to the bonding of said silicon-containing compounds, the surface active agent has enough time to migrate out to the surface of the fibrous structure to secure an immediate first inlet. However, it is important in the case of internal additives that the bonding of said silicon-containing compounds to the fibrous structure is perfomed before the internal additive has migrated to the surface, or otherwise a cleaning step is required.

Further, a fibrous structure according to the invention, exhibits excellent properties of "hydrophilicity" or "wettability" which are both immediate and durable.

In accordance with one embodiment, the silicon-containing compound is mainly constituted of a compound of the type $SiO_xH_y$ wherein x preferably is in the range of 1 to 4, and y preferably in the range of 0 to 4.

An advantage with a fibrous structure of this type is that the wetting characteristics of the structure has proved to be substantially constant during wetting and that the fibrous structure is comparatively resistant to ageing.

As already mentioned, the fibrous structures in accordance with the invention exhibit at least one polar silicon-containing material surface, or portion of a surface and wherein a surface active agent or a composition comprising a surface active agent is added to the fibrous structure. However, it is possible according to the invention to apply silicon-containing compounds, and wherein a surface active agent or a composition comprising a surface active agent is added to both surfaces of a sheet of material. Further, one or both surfaces of the material may exhibit one or more delimited areas having polar silicon-containing compounds and wherein a surface active agent or a composition comprising a surface active agent is added.

According to one fibrous structure of the invention, said fibrous structure consists of one or more non-woven materials. According to one further aspect of the invention, the fibrous structure may, for instance, be used as fluid permeable cover sheet for absorbent articles or as a fluid transfer layer between the fluid permeable cover sheet and the absorbent structure (absorption body) in an absorbent article, or for the absorbent structure itself.

The invention additionally relates to a fibrous structure for use in an absorbent article such as a diaper, an incontinence guard, a sanitary napkin, wipe or the like, said absorbent article comprises an absorption body being enclosed between a fluid impermeable cover layer and a fluid permeable cover layer (fluid permeable cover sheet), said article comprising at least one portion comprising a fibrous structure as described herein.

Further the fibrous structure may be used for tissue products. As well known to the man skilled in the art, the term "tissue" commonly covers fibrous material based on cellulose or cellulose in combination with synthetic fibres. Tissue are typically used in the manufacture of household items such as kitchen towels, toilet paper, napkins or wipes, in the manufacture of layers entering the structure of absorbent articles such as diapers, incontinence guards, sanitary napkins, or the like.

The present invention also relates to a fibrous structure as described herein, wherein said fibrous structure constitutes a fluid permeable cover sheet, or one or more layers of a multi-layered fluid permeable cover sheet of an absorbent article.

In accordance with one embodiment, the treatment, besides the addition of surface active agent or a composition comprising a surface active agent, is based on a electrical discharge led in a gaseous mixture, leading to the formation of a plasma.

As well known, a plasma is a gaseous medium containing ions, radicals, electrons, excited, metastable and unstable species. It can be obtained through supplying to a gaseous mixture a sufficient amount of energy, at a defined pressure, for example very low pressure or atmospheric pressure.

All the species of the plasma can react between them and/or with the components of the gaseous mixture to create new ions, radicals, and excited species.

When it is carried out at atmospheric pressure with a high voltage electrical energy supply, the plasma is commonly called "corona".

According to this embodiment, the fibrous structure has been submitted to an electrical discharge, in presence of a gaseous mixture comprising at least one type of silicon-containing compound, oxygen or other oxygen-containing gas, and a carrier gas.

In a further embodiment the fibrous structure has been submitted to a treatment atmosphere as-obtained in post-discharge of an electrical discharge applied to a gaseous mixture comprising at least one type of silicon-containing compound, oxygen or other oxygen-containing gas, and a carrier gas.

In any case, the unstable and excited species of the atmosphere react with the polymer chains of the surface of the fibrous structure, leading to the formation of radicals of said polymer chains. The radicals can then react with species present in the vicinity of the radicals and thereby forming new bondings and new functional groups on the surface. Functional groups which are relevant to the present invention are polar silicon-containing groups. The functional groups which are introduced on the surface by the reaction of the radicals, are much more strongly bonded to the surface than an active substance which has been applied as a conventional coating.

A method for corona treatment is described in U.S. Pat. No. 5,576,076, U.S. Pat. No. 5,527,629 and U.S. Pat. No. 5,523,124. The gas mixture is based on a carrier gas which usually is nitrogen, a silicon-containing compound and an oxidant. The treatment creates a layer of material having an inorganic, hydrophilic surface.

The disclosed method is suitable for use in connection with the invention. However, the invention is not limited to the method described in the above mentioned applications, but comprises all types of gas phase treatments in which polar silicon-containing groups are introduced to a surface of a fibrous structure, and wherein a surface active agent or a composition comprising a surface active agent is added to the fibrous structure.

In accordance with one embodiment the silicon-containing compound in the gas mixture is a silane compound. Some examples of such compounds are $Si_nH_{2n+2}$ where n preferably is from 1 to 4, silicon hydrides, halogenated silanes, alkoxysilanes or organosilanes. The oxidant may be oxygen or other oxygen-containing gases such as, for instance, $CO$, $CO_2$, $NO$, $N_2O$ or $NO_2$. The carrier gas may consist of nitrogen, argon, helium, or any mixture thereof.

According to one embodiment of the invention, prior to being treated with the medium comprising unstable and excited species, resulting from the application of said electrical discharge in presence of said gaseous mixture comprising the silicon-containing gaseous compound, an oxidant and a carrier gas, or prior to said treatment atmosphere in post-discharge, the fibrous structure has been in a first step submitted to a corona discharge under air or under an atmosphere comprising a carrier gas and an oxidizing gas (surface preparation).

According to a further embodiment of the invention said fibrous structure, after being submitted to said electrical discharge in presence of said gaseous mixture, or to said treatment atmosphere in post-discharge, has been submitted to a post-treatment by being submitted to a corona discharge under air or under an atmosphere comprising a carrier gas and an oxidizing gas.

Still a further embodiment relates to a fibrous structure as described herein, wherein said fibrous structure exhibits a predetermined degree of hydrophilicity which is substantially unaffected by wetting of said fibrous structure.

Further, the invention relates to a fibrous structure having one or more types of polar, silicon-containing compounds bonded to at least one portion of the surface of said fibrous structure, and wherein a surface active agent or a composition comprising a surface active agent is added to the fibrous structure. The surface active agent or the composition comprising the surface active agent may be of any suitable kind as described earlier and is added for example by a conventional spraying technique, a conventional foaming technique, a conventional kiss-roll technique or is added as an internal additive.

The present invention provides a fibrous structure of the kind mentioned in the introduction, wherein said fibrous structure exhibits when desired a well defined rate of wetting, i.e. a predetermined degree of hydrophilicity which is substantially unaffected by wetting of the fibrous structure.

Furthermore, with the present invention a fibrous structure is provided having with a desired, predetermined degree of hydrophilicity which is maintained even after said fibrous structure has been stored for a period of time.

A fibrous structure, in accordance with the invention is primarily distinguished by one or several types of polar, silicon-containing compounds being bonded to at least one portion of the surface of said fibrous structure by interaction between the surface and the silicon containing compounds, and by the addition of a surface active agent or a composition comprising a surface active agent to said fibrous structure.

As previously mentioned, the fibrous structure according to the invention exhibits a predetermined degree of hydrophilicity properties which is substantially unaffected by wetting of said fibrous structure.

A further embodiment of the invention discloses a fibrous structure, as described herein, wherein said fibrous structure comprises one or more non-woven material.

The present invention also relates to use of a fibrous structure as described herein for making tissue products.

Another embodiment of the present invention relates to use of a fibrous structure, as described herein, for making a gas filtration product.

Still another embodiment of the present invention relates to use of a fibrous structure, as described herein, for making a household product.

Further, the present invention relates to a tissue product made of a fibrous structure as described herein.

Furthermore, the present invention relates to a nonwoven material made of a fibrous structure as described herein.

The present invention also provides an absorbent article comprising an absorption body and at least one fibrous structure, wherein said at least one fibrous structure is a fibrous structure according to the present invention as described earlier.

An absorbent article may be for example a hygienic article, i.e. a feminine, a medical or a surgical hygienic article, and the hygienic articles may include e.g. diapers, sanitary napkins, incontinence guards, or similar.

Further, the absorbent article which may be for example a diaper, an incontinence guard, a sanitary napkin or the like, comprises an absorption body being enclosed between a fluid impermeable cover layer and a fluid permeable cover layer, wherein said article comprises at least one portion which comprises one or more fibrous structures, wherein at least one fibrous structure is a fibrous structure according to the present invention as described earlier.

The absorption body may comprise any suitable material known to a person skilled in the art, e.g. natural materials, for example cellulosic fibres (e.g. fluffed cellulose pulp), cotton fibres, peat; synthetic materials, i.e. synthetic fibres with absorbing or liquid wicking ability; superabsorbent materials, e.g. in a form of fibres, particles, granules, film; or any suitable mixture thereof.

A superabsorbent material usually has an ability to absorb fluids in an amount corresponding to several times the weight of the superabsorbent material itself. Further, a superabsorbent material may bind any absorbed fluid and may thereby form for example a fluid-containing gel.

The absorption body may further comprise a binding agent, shape stabilizing means, or the like. It is also possible to use additional absorbent layers in order to improve the absorption properties, such as different types of liquid dispersing inserts or material layers. Further, the absorption body may be chemically or mechanically treated in order to change the absorption characteristics. A commonly employed way of improving the wicking ability of an absorbent structure is to provide the absorption body with a pattern of compressed areas. Furthermore, it is possible to use absorbent materials such as absorbent non-woven materials, absorbent foams, or the like to produce the absorption body. Likewise, all conceivable combinations of suitable absorbent materials may be used to produce the absorption body.

Further, the absorbent article may comprise one or more fibrous structures, wherein at least one fibrous structure is as described earlier, which fibrous structures optionally may be of a natural or a synthetic material, and of a woven or a non-woven type, the fibrous structures may be of, for example, polypropylene, polyethylene, polyester, or their copolymers, cellulosic or cotton fibres, peat or polylactides. The fibrous structures may also be of a non-woven material, which non-woven material is composed of two or several of the components listed herein or any mixture thereof.

Furthermore, said one or more fibrous structures, wherein said at least one fibrous structure is as described herein, may consist of one or more non-woven materials. Moreover, the fibrous structures may for instance be used as a fluid permeable cover sheet for absorbent articles or as a fluid transfer layer between the fluid permeable cover sheet and an absorbent structure (the absorption body) in an absorbent article, or for the absorbent structure itself. Further, said one or more fibrous structures, wherein said at least one fibrous structure is as described herein, may constitute a part or all of the fluid pervious cover layer and/or of a fluid transfer layer positioned between the fluid pervious cover layer and the absorption body. Still further, the fibrous structures may comprise one or more tissue layers.

However, said at least one fibrous structure, as described herein, is initially hydrophobic and has been treated to be hydrophilic.

Further, said fibrous structure according to the present invention, or said at least one fibrous structure which is comprised in said absorbent article of the present invention, may be tested in a series of run-off tests according to EDANA run-off method number 152.0-99, wherein each run-off test comprises a volume a test solution, wherein the test solution may be, for example, test solution 1 which will be described later. The run-off in percent by weight, i.e. run-off level, for each tested fibrous structure is determined by the run-off test.

According to one embodiment the run-off test is performed by pouring a determined amount, here with a volume of 25 ml, of test solution 1 at a flow rate of 7 ml/s and from a height of 25 mm onto an inclined fibrous structure. The fibrous structure is placed on top of three layers of filter paper on an inclined table and the inclination is 25°. The length of each tested fibrous structure from the point where the test solution 1 is inserted to the end of the fibrous structure in the run-off direction is 260 mm. The amount of fluid, test solution 1, which run off the fibrous structure is collected and weighed. Throughout a series of run-off tests the run-off test is repeated five times on the same fibrous structure with a four minutes interval, i.e. the series starts with a first run-off test and ends with a fifth run-off test. The run-off is measured five times after each other on the same fibrous structure. The three layers of filter paper are replaced after each run-off test in the series.

Further, the test solution 1 is a 0.9% by weight saline (NaCl) solution and said test solution 1 has a surface tension which is above $70*10^{-3}$ N/m before the first run-off test. However, after the first run-off test said test solution 1 has a surface tension which is less than $60*10^{-3}$ N/m, which means that the fibrous structure of the present invention decreases the surface tension of said test solution 1.

Further, an absorbent article according to the invention, exhibits excellent properties of "hydrophilicity" or "wettability" which are both immediate and durable.

A further embodiment of the present invention relates to an absorbent article, wherein said at least one fibrous structure constitutes a fluid permeable cover sheet, or one or more layers of a multilayered fluid permeable cover sheet.

The present invention also relates to an absorbent article, as described herein, wherein said absorbent article is being used for making a wipping article.

An further embodiment relates to an absorbent, wherein said absorbent article is being used for making an hygiene article.

Moreover, the present invention also relates to an absorbent article comprising an absorption body and said at least one fibrous structure, which absorbent article may be tested in a series of run-off tests, wherein each run-off test comprises exposing said absorbent article to a volume of a test solution. The test solution may be, for example, test solution 2, which will be described later. Said absorbent article exhibits a run-off level that is less than seven percent by weight throughout a series of run-off tests, wherein the series starts with a first run-off test and ends with a fifth run-off test and wherein said volume is from 80 to 120 ml.

The absorbent article may be of any kind as defined above. However, each absorbent article which is used in the example described herein comprises from top to bottom: a fluid permeable cover sheet (nonwoven polypropylene, 18 g/m$^2$), a wadding (nonwoven material, 50 g/m$^2$), a small core (pulp-CTMP and superabsorbent powder), a big core (pulp-CP and superabsorbent powder) and a plastic film. Wherein said fluid permeable cover sheet corresponds to said at least one fibrous structure. Moreover, said fluid permeable cover sheet and said plastic film of said absorbent article are welded, glued or by any method obvious to a person skilled in the art joined together at the edges.

Said at least one fibrous structure may constitute for example a fluid permeable cover sheet, one or more layers of a multi-layered fluid permeable cover sheet, e.g. an upper and/or a lower fluid transfer layer, or similar of any suitable absorbent article. Further, said at least one fibrous structure which initially is hydrophobic and has been treated to act hydrophilic is accomplished as described earlier.

In order to determine percent by weight run-off for an absorbent article a run-off test described below was used. By the run-off test the amount of non-absorbed fluid (e.g. test solution 2) is measured when a determined amount (80 ml) of the test solution, which may be, for example, test solution 2, is poured onto the absorbent article from a distance of 7 mm perpendicular to the surface of the absorbent article and at a flow rate of 30 ml/s. The test solution is poured onto the absorbent article by use of a dosage tube having an inclination of 20° to the absorbent article, which dosage tube includes a "spreading plate" to simulate a real case scenario.

Prior to the run-off test a piece having the size 120 mm×400 mm is cut out from the absorbent article which is intended to be tested and said piece is placed onto an inclined table having an inclination of 45°. The length of each tested absorbent article from the point where the test solution is inserted to the end of the absorbent article in the run-off direction is 150 mm.

The amount of the test solution which is not absorbed by the absorbent article, i.e. the run-off, is collected and weighed. The run-off test is repeated five times on the same absorbent article with a ten minutes interval. The run-off is weighed after each run-off test. Thus, the run-off is measured five times after each other on the same absorbent article in a series of run-off tests wherein the series starts with a first run-off test and ends with a fifth run-off test.

The test solution 2 which may be used in the test method is synthetic urine which contains $MgSO_4$ 0.66 g/l, KCl 4.47 g/l, NaCl 7.60 g/l, $NH_2CONH_2$ 18.00 g/l, $KH_2PO_4$ 3.54 g/l, $Na_2HPO_4$ 0.745 g/l, Triton X-100 (0.1%) 1.00 g/l and a 10% Nykockin solution in deionized water 0.4 g/l.

Moreover, the present invention also relates to an absorbent article testable in the described run-off test and wherein said run-off level that is less than five percent by weight.

Further according to the present invention, an absorbent article comprises at least one fibrous structure and said absorbent article exhibits the afore-mentioned run-off level throughout said series of run-off tests, wherein said at least one fibrous structure has been accomplished as described earlier.

The present invention also provides an absorbent article of the kind mentioned in the introduction comprising at least one fibrous structure, wherein said fibrous structure exhibits when desired a well defined rate of wetting, i.e. a predetermined degree of hydrophilicity which is substantially unaffected by wetting of the fibrous structure.

Furthermore, with the present invention an absorbent article is provided having at least one fibrous structure with a desired, predetermined degree of hydrophilicity which is maintained in said fibrous structure even after the article has been stored for a period of time. Accordingly, the present invention offers an absorbent article, i.e. a hygienic article, having a well defined and controlled course of wetting.

An absorbent article, which comprises at least one fibrous structure, in accordance with the invention is primarily distinguished by one or several types of polar, silicon-containing compounds being bonded to at least one portion of the surface of said at least one fibrous structure by interaction between the surface and the silicon containing compounds, and by the addition of a surface active agent or a composition comprising a surface active agent to said at least one fibrous structure.

As previously mentioned, the absorbent article according to the invention exhibits by said at least one fibrous structure a predetermined degree of hydrophilicity properties which is substantially unaffected by wetting of said fibrous structure.

An advantage with a fibrous structure of this type is that the wetting characteristics of the structure has proved to be substantially constant during wetting and that the fibrous structure is comparatively resistant to ageing.

As already mentioned, the fibrous structures in accordance with the invention exhibit at least one polar silicon-containing material surface, or portion of a surface and wherein a surface active agent or a composition comprising a surface active agent is added to the fibrous structure. However, it is possible according to the invention to apply silicon-containing compounds, and wherein a surface active agent or a composition comprising a surface active agent is added to both surfaces of a sheet of material. Further, one or both surfaces of the material may exhibit one or more delimited areas having polar silicon-containing compounds and wherein a surface active agent or a composition comprising a surface active agent is added.

According to one absorbent article of the invention, the fibrous structure consists of one or more non-woven materials. According to one further aspect of the invention, the fibrous structure may, for instance, be used as fluid permeable cover sheet for absorbent articles or as a fluid transfer layer between the fluid permeable cover sheet and the absorbent structure (absorption body) in an absorbent article, or for the absorbent structure itself.

The invention additionally relates to an absorbent article such as a diaper, an incontinence guard, a sanitary napkin or the like comprising an absorption body being enclosed between a fluid impermeable cover layer and a fluid permeable cover layer (fluid permeable cover sheet), said article comprising at least one portion comprising a fibrous structure as described herein.

In an absorbent article according to the invention said at least one fibrous structure may constitute a part or all of the fluid pervious cover layer and/or of a fluid transfer layer positioned between the fluid pervious cover layer and the absorption body.

In an absorbent article, i.e. a hygienic product, for fluid absorption purposes and being constructed from a plurality of individual layers, fluid transfer between the different layers is of great importance both for the rate of wicking within each individual layer and for the total fluid uptake capacity of the hygienic product. From the above discussion it appears that in fluid absorbent articles of this kind it is very important that all layers of material exhibit a well-defined and stable degree of hydrophilicity which varies only to a very limited extent with wetting and ageing.

The present invention also relates to an absorbent article as described herein, wherein said at least one fibrous structure constitutes a fluid permeable cover sheet, or one or more layers of a multi-layered fluid permeable cover sheet.

According to one of the aspects of the invention, a liquid permeable cover sheet, a fluid transfer layer, and/or an absorption body of an absorbent article have different degrees of hydrophilicity.

According to one embodiment of the invention, the fluid transfer layer of the hygiene article comprises a set of several fibrous structures according to the invention, the set of fibrous structures presenting a gradient of degrees of hydrophilicity.

In accordance with one embodiment of said absorbent article, the treatment of said at least one fibrous structure, besides the addition of surface active agent or a composition comprising a surface active agent, is -based on a electrical discharge led in a gaseous mixture, leading to the formation of a plasma, as described earlier for said fibrous structure.

Other characteristics and advantages of the present invention will become apparent from the following detailed description of some of the embodiments thereof in connection with the appended drawings.

SHORT DESCRIPTION OF FIGURES

The invention will in the following be described in greater detail with reference to the embodiment which is shown in the appended drawing.

Figure 2:
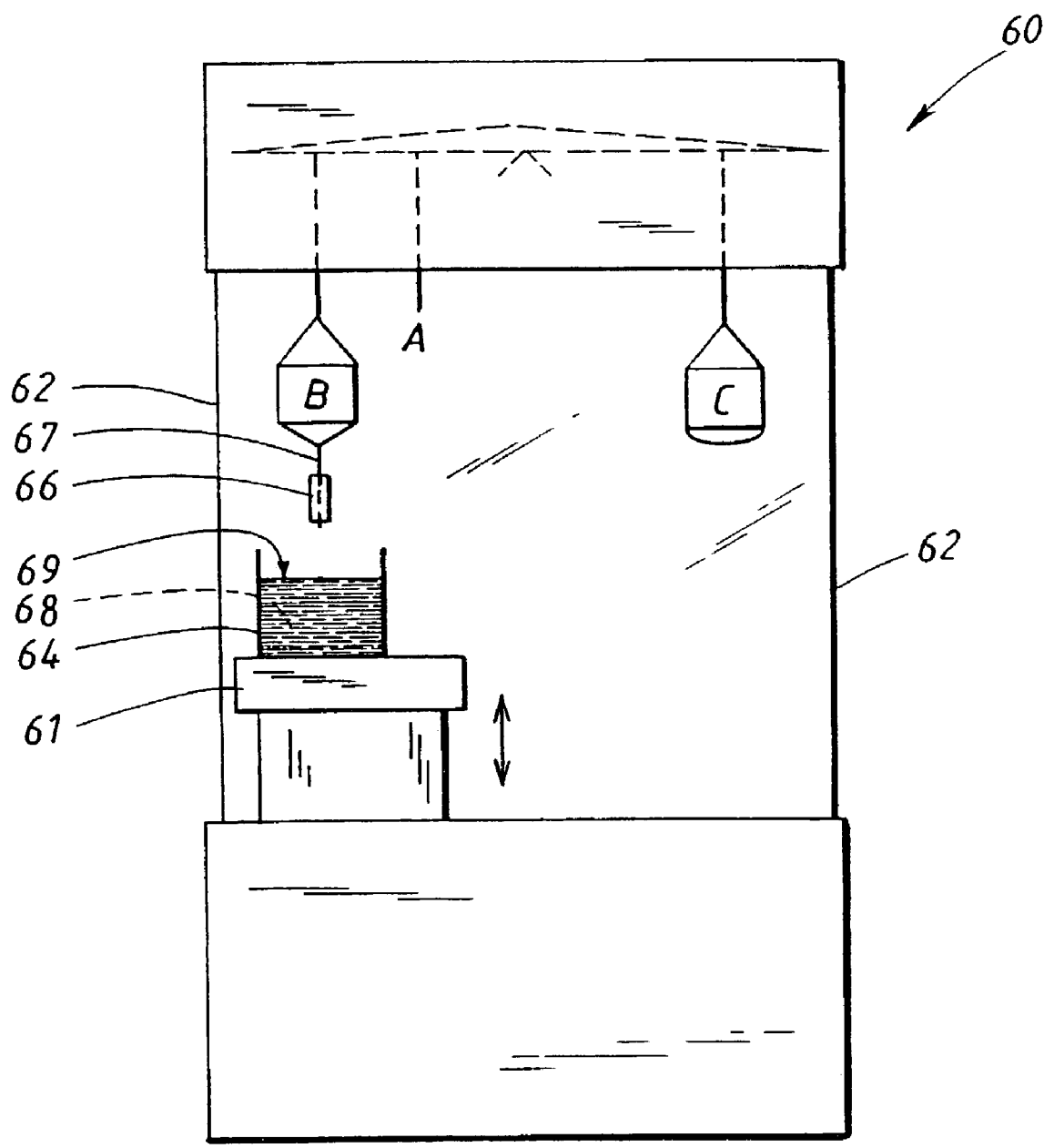

FIG. 1 shows a diaper seen from the side which is intended to be facing a user during use FIG. 2 shows means for determining the surface tension (i.e. surface energy) of a test-solution

DESCRIPTION OF EMBODIMENTS AND EXAMPLES

The diaper 100 which is shown in FIG. 1 comprises a fluid permeable cover sheet 101, a fluid impermeable cover sheet 103 and an absorption body 105 enclosed between the cover sheets 101, 103. The fluid impermeable cover sheet 103 may consist of a fluid impermeable plastic film, a sheet of non-woven material which has been provided with a fluid resistant coating or any other type of flexible sheet material which resists fluid penetration. Generally, it is an advantage if the fluid impermeable cover sheet 103 is breathable at least to some extent, implying that water vapour may pass through the cover sheet.

The covering sheets 101, 103 have a planar extension which is somewhat greater than the planar extension of the absorption body 105 and comprise edge portions 107 which protrude beyond the peripheral edge of the absorption body 105. The cover sheets 101, 103 are joined within the protruding edge portions 107 by means of, for instance, adhesive or welding with heat or ultrasonically.

Further, the diaper 100 has two longitudinally extending side edges 123, 125, a front end edge 109 and a rear end edge 111, and exhibits a front portion 113, a rear portion 115, and an intermediate crotch portion 117 which is narrower than the end portions 113, 115.

In addition, elastic elements 119, 121 are arranged along the side edges 123, 125 at the crotch portion 117 of the diaper. The purpose of the elastic elements 119, 121 is to provide a means for keeping the diaper in sealing contact around the legs of a user when the diaper is being worn. An additional elastic element 127 is arranged along the rear end edge 111 and is provided in order to give the diaper 100 a certain degree of extensibility and conformability and to act as a sealing means against waist leakage.

A tape tab 129, 131 is arranged at each side edge 123, 125 close to the rear end edge 111. The tape tabs 129, 131 constitute fastening means for the diaper 100 and permit the diaper 100 to be formed into a garment enclosing the lower part of the wearer's body in a manner similar to that of a pair of underpants. The tape tabs 129, 131 cooperate with a receiving area 133 arranged on the fluid impermeable cover sheet 103 at the front portion 113 of the diaper. The receiving area 133 may be constituted by a reinforcing material which has been laminated to the fluid impermeable cover sheet 103. By reinforcing the cover sheet the diaper 100 may be closed and reopened without affecting the adhesive properties of the tape tabs 129, 131 or causing the fluid impermeable cover sheet 103 to rupture.

It is, of course, possible to use any of a number of different alternative types of fastening elements for the diaper 100. Some examples of such alternative fastening elements are hook-and-loop surfaces, press studs, tying ribbons, buttons, or similar.

The absorption body 105 usually comprises one or more layers of cellulose fibres, such as fluffed cellulose pulp. In addition to cellulosic fibres the absorption body 105 may comprise superabsorbent material which is a material in the form of fibres, particles, granules, film or the like and which has the ability to absorb fluid in an amount corresponding to several times the weight of the superabsorbent material itself. Superabsorbent materials bind the absorbed liquid and form a liquid-containing gel.

The absorption body 105 may further comprise a binding agent, shape stabilizing means, or the like. It is also possible to use additional absorbent layers in order to improve the absorption properties, such as different types of liquid dispersing inserts or material layers. The absorption body 105 may be chemically or mechanically treated in order to change the absorption characteristics. A commonly employed way of improving the wicking ability of an absorbent structure is to provide the absorption body with a pattern of compressed areas. Furthermore, it is possible to use absorbent materials such as absorbent non-woven materials, absorbent foams, or the like. Likewise, all conceivable combinations of suitable absorbent materials may be used.

The fluid permeable cover layer (fluid permeable cover sheet) 101 comprises one or more layers of material wherein at least one layer of material consists of a fibrous structure in accordance with the invention. A fibrous structure in accordance with the invention can enter the structure of an upper layer 106 which during use of the diaper 100 will be in contact with the body of the user and/or a lower fluid transfer layer 108 which is situated between the upper, skin-contacting layer 106 and the absorption body 105 which is arranged beneath the fluid permeable cover layer (fluid permeable cover sheet) 101 and/or the absorption body 105. Further, a fibrous structure according to the invention is either a bonded nonwoven layer, an unbonded, porous fibre wadding, or both. Moreover, fibrous structures comprising cut staple fibres and/or continuous filaments (i.e. tow) are conceivable with the embodiments of the invention. In case of both the upper, skin-contacting layer 106, the absorption body 105, and the fluid transfer layer 108 being fibrous structures in accordance with the invention it is advantageous if the layers 106,108 and/or the absorption body 105 exhibit mutually different degrees of hydrophilicity. This may, for instance, be achieved by using gas mixtures of different composition when treating the different fibrous structures and/or by the addition of a surface active agent or a composition comprising a surface active agent to the fibrous structure.

The invention is not restricted to any particular type of material. Accordingly, the choice of polymer, fibre thickness or density of fibres is dependent on the type of article, e.g. absorbent article, for which the fibrous structure is intended as well as the function and location of the fibrous structure in the article (searching for hydrophilicity properties). By way of illustration, fibrous structures are commonly made of polypropylene, polyethylene, polyester, and their co-polymers. However, the invention should not be restricted to these polymers. One example of another type of useful polymers is biodegradeable polymers such as polylactides. In order for biodegradeable materials such as materials containing polylactides to perform well as a fluid pervious cover sheet it is usually necessary to treat the material with a hydrophilic agent.

Moreover according to the invention, said bonding of one or more types of polar, silicon-containing compounds to at least one portion of the surface of said fibrous structure increases the surface energy of said fibrous structure, which renders less migration of the added surface active agent or the composition comprising a surface active agent due to a higher affinity/attraction of the added surface active agent or the composition comprising a surface active agent to the more polar surface of said fibrous structure, and as a consequence of said less migration giving fibrous structures and absorbent article less sensitive to ageing.

Furthermore, a smaller amount of surface active agent or a composition comprising a surface active agent can be used, and/or a more homogeneously "coated" fibrous structure can be obtained.

Further, as it is possible according to the present invention, to delimit said addition of a surface active agent or a composition comprising a surface active agent, it is also possible to delimit any problems related to migration for example skin irritation, influence of any absorption bodies, or ageing of said absorbent articles.

Accordingly, the present invention provides a means for creating e.g. a fluid permeable cover sheet which, besides exhibiting excellent properties of "hydrophilicity" or "wettability" which are both immediate and durable, does not show any of or at least significantly reducing the problems related to conventional surface active agent treatment or to commonly used corona treatment (optionally in combination with addition of hydrophilic substances) described in the background art, because of said bonding of one or more types of polar, silicon-containing compounds and said addition of a surface active agent or a composition comprising a surface active agent.

EXAMPLE 1

Preparation of Fibrous Structures

In the samples 1A-E below the fibrous structures comprise a non-woven polypropylene with a basis weight of 18 g/m².
1A. polypropylene non-woven material which has been treated with surface active agent
1B. polypropylene non-woven material which has been corona treated with a conventional method and surface active agent is added to the material
1C. polypropylene non-woven material which has been corona treated in order to introduce polar silicon-containing groups to the surface of the material and surface active agent is added to the material
1D. polypropylene non-woven material and 0.23 weight % of surface active agent is added to the material
1E. polypropylene non-woven material which has been corona treated in order to introduce polar silicon-containing groups to the surface of the material
1F. polypropylene non-woven material which has been corona treated in order to introduce polar silicon-containing groups to the surface of the material and 0.14 weight % of surface active agent is added to the material Sample 1B was here treated in one step: corona treated under air.

The operating conditions under which the sample 1B was treated according to the invention are as follows:
Speed of the web (the fibrous structure)=22 m/min
Width of the electrode=0.65 m
Electrical power of corona=1720 W The operating conditions under which the samples 1C, 1E and 1F were treated according to the invention are as follows:
Speed of the web (the fibrous structure)=25 m/min
Width of the electrode=0.65 m
Electrical power of corona=1463 W
Flow rate of $N_2$=166 l/min
Flow rate of $N_2O$=0.38 l/min
Flow rate of $SiH_4$=0.110 l/min Samples 1C, 1E and 1F were treated in two steps: in a first step, corona treated under air, and in a second step, corona treated with injection of the above described gaseous mixture of $N_2$, $N_2O$ and $SiH_4$.

Further, to samples 1A, 1B and 1C a surface active agent (an organosilicon based surfactant with trade name Nuwet 237) was added by spraying a 0.5 weight % water solution of the surface active agent to the fibrous structures by a conventional spraying technique, to give samples having 1.0±0.2 weight % of the surface active agent calculated on dry weight of said samples. The amount of surface active agent added to samples 1A, 1B and 1C was measured by an "Extraction method".

Said "Extraction method" comprises the following steps: Weighing 8.0 g of the sample, and adding said 8.0 g of the sample and 200 ml isopropanol to a pre-weighed beaker. Stirring every fifteen minute and letting the sample and the isopropanol be in the beaker for one hour at room-temperature. Wringing out the isopropanol from the sample and moving the sample from the beaker. Letting the isopropanol in the beaker evaporate and weighing the beaker giving the amount of surface active agent. Further, letting the sample dry and weighing the sample giving the dry weight of the sample.

Moreover, sample 1D is a commercially available material which has 0.23 weight % of a surface active agent (an organosilicon based surfactant with trade name Nuwet 237) added, to sample 1E there was no surface active agent added, and to sample 1F 0.14 weight % of a surface active agent (an organosilicon based surfactant with trade name Nuwet 237) was added by using a kiss-roll technique. The amount of surface active agent added to samples 1D and 1F was measured by a "Wet Pick-Up"-method and is given as weight % of dry weight of said samples. The "Wet Pick-Up"-method involves weighing the dry and the wet sample. The wet sample is weighed directly after application of the surfactant solution to the sample. Knowing the concentration of the surfactant solution, the weight of the applied surfactant can be calculated.

After the addition of surface active agent, samples 1A, 1B, 1C, 1D and 1F were dried.

EXAMPLE 2

Determination of Run-off Level in Percent by Weight Run-off for a Fibrous Structure Percent by weight run-off of samples 1A, 1B and 1C were determined in a first round, and percent by weight run-off of samples 1D, 1E and 1F were determined in a second round.

In order to determine percent by weight run-off for a fibrous structure a run-off test, the EDANA test method no. 152.0-99, was used. By the run-off test the amount of non-absorbed fluid (test solution 1) is measured when a determined amount, volume is 25 ml, of the test solution 1 is poured onto the fibrous structure from a height of 25 mm and at a flow rate of 7 ml/s.

Samples of the fibrous structures, non-woven polypropylene with a basis weight of 18 g/m², 140×285 mm is prepared by cutting and the long side is in the machine direction. The fibrous structure is fixed and placed on top of three layers of filter paper (FFS filter paper 140×280 mm from Hollingsworth & Vose Company Ltd) on an inclined table and the inclination is 25°. The length of each tested fibrous structure from the point where the test solution 1 is inserted to the end of the fibrous structure in the run-off direction is 260 mm.

The amount of the test solution 1 which is not absorbed by the fibrous structure, i.e. the run-off, is collected and weighed. The run-off test is repeated five times on the same fibrous structure with a four minutes interval. The run-off is weighed after each run-off test. Thus, the run-off is measured five times after each other on the same fibrous structure in a series of run-off tests wherein the series starts with a first run-off test and ends with a fifth run-off test. The three layers of filter paper is replaced after each run-off test in the series.

The test solution 1 used in the test method is a 0.9 weight percent (NaCl) saline solution having a surface tension above $70*10^{-3}$ N/m before the first run-off test.

Result of Example 2—Run-off Level

First Round

| Sample | Run-off (% weight) | | | | |
| --- | --- | --- | --- | --- | --- |
| | 1st test | 2nd test | 3rd test | 4th test | 5th test |
| 1A | 0 | 1 | 16 | 56 | 74 |
| 1B | 0 | 0 | 4 | 18 | 55 |
| 1C | 0 | 0 | 0 | 0 | 0 |

Second Round

| | Run-off (% weight) | | | | |
|---|---|---|---|---|---|
| Sample | 1st test | 2nd test | 3rd test | 4th test | 5th test |
| 1D | 0 | 4 | 41 | 72 | 64 |
| 1E | 71 | 60 | 33 | 31 | 23 |
| 1F | 0 | 0 | 0 | 0 | 0 |

EXAMPLE 3

Determination of Surface Tension of Test Solution 1

The surface tension (i.e. surface energy) of the test-solution was determined by means of the apparatus shown in FIG. 2. Thereby, Wilhelmy's method was used.

The balance which was used for the determination of the surface tension in connection with the invention, is manufactured by Cahn instruments in California. The model number is DCA-322, where DCA stands for "Dynamic Contact Angle". A PC, IBM300PL, was used for controlling the instrument. The same computer was also utilized for recording data from the measurements and for performing the subsequent calculations.

Before measuring, a lamina of glass 66 is properly cleaned by burning in a flame. During the measurement, the lamina of glass 66 is vertically suspended in an extremely sensitive balance 60. A liquid container 64 is placed on a mobile table 61, directly below the lamina of glass 66. When the lamina of glass 66 is dipped into the liquid 68, a liquid meniscus, which affects the partially immersed lamina with a vertical force, is formed around the lamina.

The force is measured by means of the balance. The force is related to the surface tension according to:

$$F = \gamma p \cos \theta + mg - \rho_L lgA$$

F=the measured force (N)
γ=the surface tension (i.e. surface energy) of the liquid (N/m)
p=the circumference of the fibre (m)
θ=the contact angle in the interface solid (lamina of glass)/liquid
m=the mass of the solid (kg)
g=the constant of gravitation (m/s2)
$\rho_L$=the density of the liquid (kg/m3)
I=the depth of immersion of the solid (m)
A=the cross-sectional area of the solid (m3)

The second term in the equation represents the weight of the glass lamina, while the third term of the equation is the so-called "buoyancy-force", i.e. the weight loss which arises as a result of displaced liquid volume. In a computer (not shown) furnished with a calculation program for surface tension determination, both these two terms are taken into account, something which simplifies the equation to:

$$F = \gamma p \cos \theta$$

The surface tension of the liquid is obtained by measuring the force when the lamina is lifted up from the liquid.

The mobile table 61 is elevated and lowered with a constant speed (150 μm/s). Furthermore, the temperature in the sample chamber should be controlled.

The balance 60 has three pans (see FIG. 2). The pan B with an accuracy of $10^{-5}$ g, is used for surface tension (surface energy) measurements on liquids. The balance is tared by means of placing counterweights in a third pan C.

In order to prevent draughts, dust, or the like, from disturbing the measurement, the pans and the mobile table 61 are protected by sliding glass frames 62. These also enable control of air moisture and temperature. In order to avoid disturbing vibrations during the course of the measurement, the balance is placed on a foundation (not shown).

The table which the liquid container 64 stands on is elevated and lowered by means of a motor (not shown). The speed of the table 61 is controlled by the connected computer and is displayed before a measurement is started. Other parameters which have to be fed in before the measurement is started are the maximal depth of immersion and the perimeter of the glass lamina. The software of the computer uses a contact angle of zero for surface tension (surface energy) calculation of liquids.

The balance 60 has first been tared with the metal clamp 67 and the lamina being suspended in the pan B. Test liquid 68, is placed in the liquid container 64 on the table 61 below the lamina. The lamina should be suspended perpendicular to the liquid surface 69 and has to be completely still before the measurement starts so that the balance shows a stable value. The table 61 with the liquid container 64 is elevated manually so that the liquid surface 69 is approximately 1 mm from the lamina.

When the measurement is started, the computer records a base line, whereafter the table 61 is elevated with a predetermined speed. When the maximal depth of immersion is reached, the computer is commanded to lower the table.

The surface tension was determined for test solution 1 after a first run-off test on sample 1D, 1E and 1F respectively. Said first run-off test was achieved as in Example 2 above with the exception that there was no filter paper used, thus enabling collection of test solution after first run-off test.

1D. polypropylene non-woven material and 0.23 weight % of surface active agent is added to the material
1E. polypropylene non-woven material which has been corona treated in order to introduce polar silicon-containing groups to the surface of the material
1F. polypropylene non-woven material which has been corona treated in order to introduce polar silicon-containing groups to the surface of the material and 0.14 weight % of surface active agent is added to the material Results of Example 3—Surface Tension (i.e. Surface Energy) of the Liquid (N/m)

| Sample | surface tension (N/m) |
|---|---|
| 1D | $51 * 10^{-3}$ |
| 1E | $71 * 10^{-3}$ |
| 1F | $53 * 10^{-3}$ |

Before said first run-off test, the surface tension of test solution 1 is above $70*10^{-3}$ N/m.

EXAMPLE 4

Determination of Run-off Level in Percent by Weight Run-off for an Absorbent Article Comprising a Fibrous Structure Three absorbent articles were tested, absorbent article 2D, which comprises a fibrous structure according to sample 1D above, absorbent article 2E which comprises a fibrous structure according to sample 1E above, and absorbent article 2F which comprises a fibrous structure according to sample 1F above. Each fibrous structure forms a fluid permeable cover sheet to the corresponding absorbent article. The three absorbent articles were identical except for said fluid permeable cover sheet, and each absorbent article comprises from top to bottom: a fluid permeable cover sheet (nonwoven polypropylene, 18 g/m2), a wadding (nonwoven material, 50 g/m2), a small core (pulp-CTMP and superabsorbent powder), a big core (pulp-CP and superabsorbent powder) and a plastic film. Said fluid permeable cover sheet and said plastic film are welded, glued or by any method obvious to a person skilled in the art joined together at the edges.

Percent by weight run-off of absorbent articles 2D, 2E and 2F were determined. In order to determine percent by weight run-off for an absorbent article a run-off test was used. By the run-off test the amount of non-absorbed fluid (test solution 2) is measured when a determined amount, volume is 80 ml, of the test solution 2 is poured onto the absorbent article from a distance of 7 mm perpendicular to the surface of the absorbent article and at a flow rate of 30 ml/s. The test solution is poured onto the absorbent article by use of a dosage tube having an inclination of 20° to the absorbent article, which dosage tube includes a "spreading plate" to simulate a real case scenario.

Prior to the run-off test a piece having the size 120 mm×400 mm is cut out from the absorbent article which is intended to be tested and said piece is placed onto an inclined table having an inclination of 45°. The length of each tested absorbent article from the point where the test solution 2 is inserted to the end of the absorbent article in the run-off direction is 150 mm.

The amount of the test solution 2, which is not absorbed by the absorbent article, i.e. the run-off, is collected and weighed. The run-off test is repeated five times on the same absorbent article with a ten minutes interval. The run-off is weighed after each run-off test. Thus, the run-off is measured five times after each other on the same absorbent article in a series of run-off tests wherein the series starts with a first run-off test and ends with a fifth run-off test.

The test solution 2 used in the test method is synthetic urine which contains $MgSO_4$ 0.66 g/l, KCl 4.47 g/l, NaCl 7.60 g/l, $NH_2CONH_2$ 18.00 g/l, $KH_2PO_4$ 3.54 g/l, $Na_2HPO_4$ 0.745 g/l, Triton X-100 (0.1%) 1.00 g/l and a 10% Nykockin solution in deionized water 0.4 g/l.

Results of Example 4—Run-off Level

| Absorbent article | Run-off (% weight) | | | | |
|---|---|---|---|---|---|
| | 1st test | 2nd test | 3rd test | 4th test | 5th test |
| 2D | 3 | 36 | 62 | 67 | 68 |
| 2E | 83 | 53 | 45 | 36 | 24 |
| 2F | 1 | 1 | 4 | 2 | 2 |

The invention shall not be regarded as being restricted to the embodiments which have been described herein. Accordingly, a plurality of further variants and modifications are conceivable within the scope of the appended claims.

Therefore, if the invention and all its advantages have been particularly described and illustrated in the case of non-woven fibrous structures, and in the case of absorbent articles, as will be clearly apparent to the man skilled in the art, the invention finds a much larger field of application, including absorbent articles comprising for example woven fibrous structures, of either the natural or synthetic type.

The invention claimed is:

1. A fibrous hydrophobic structure treated to be rendered hydrophilic and exhibiting a run-off level determined by a series of run-off tests, wherein each run-off test comprises exposing said fibrous structure to a volume of 25 ml of a test solution and said fibrous structure initially is hydrophobic and has been treated to be hydrophilic, characterized in that said fibrous structure exhibits a run-off level that is zero throughout a series of run-off tests, wherein the series starts with a first run-off test and ends with a fifth run-off test, and that said test solution has a surface tension before the first run-off test which is above $70*10^{-3}$ N/m and a surface tension after the first run-off test which is less than $60*10^{-3}$ N/m, characterized in that said treatment and run-off level has been accomplished by subjecting the fibrous structure to a corona discharge in the presence of a gaseous mixture comprising i) at least one type of silicon-containing compound, ii) oxygen or other oxygen containing gas and iii) a carrier gas so as to bond one or more types of polar, silicon-containing compounds, to at least one portion of the surface of the fibrous structure and then adding an organosilicon based surface active agent or a composition comprising an organosilicon based surface active agent to the fibrous structure, and the at least one type of silicon-containing compound in the treated structure is mainly constituted of a compound of the type $SiO_xH_y$, wherein x is in the range of 1 to 4, and y in the range of 0 to 4.

2. A fibrous structure according to claim 1, characterized in that said run-off level has been accomplished by bonding one or more types of polar, silicon-containing compounds, to at least one portion of the surface of the fibrous structure.

3. A fibrous structure according to claim 1, characterized in that said corona treatment further comprises, prior to being exposed to said corona discharge in the presence of said gaseous mixture, a first step of exposing the fibrous structure to a corona discharge under air or under an atmosphere comprising a carrier gas and an oxidizing gas.

4. A fibrous structure according to claim 1, characterized in that said fibrous structure exhibits a predetermined degree of hydrophilicity which is substantially unaffected by wetting of said fibrous structure.

5. A tissue product made of a fibrous structure according to claim 1.

6. A nonwoven material made of a fibrous structure according to claim 1.

7. An absorbent article comprising an absorption body of and at least one said fibrous structure of claim 1.

8. An absorbent article according to claim 7, characterized in that said at least one fibrous structure constitutes a fluid permeable cover sheet, or one or more layers of a multilayered fluid permeable cover sheet.

9. An absorbent article according to claim 7, being testable in a series of run-off tests, characterized in that each run-off test comprises exposing said absorbent article to a volume of test-solution, wherein said absorbent article exhibits a run-off level that is less than seven percent by weight throughout a series of run-off tests, wherein the series starts with a first run-off test and ends with a fifth run-off test and wherein said volume is 80 ml.

10. An absorbent article according to claim 9, characterized in that said run-off level is less than five percent.

11. A fibrous hydrophobic structure treated to be rendered hydrophilic and exhibiting a run-off level determined by a series of run-off tests, wherein each run-off test comprises exposing said fibrous structure to a volume, of 25 ml of a test solution and said fibrous structure initially is hydrophobic and has been treated to be hydrophilic, characterized in that said fibrous structure exhibits a run-off level that is zero throughout a series of run-off tests, wherein the series starts with a first run-off test and ends with a fifth run-off test, and that said test solution has a surface tension before the first run-off test which is above $70*10^{-3}$ N/m and a surface tension after the first run-off test which is less than $60*10^{-3}$ N/m, characterized in that said run-off level has been accomplished by adding to the fibrous structure an organosilicon based surface active agent or a composition comprising a surface active agent, and then bonding one or more types of polar, silicon-containing compounds, to at least one portion of the surface of the fibrous structure by exposing the surface to a corona discharge in the presence of a gas mixture comprising i) at least one type of silicon-containing compound, ii) oxygen or other oxygen containing gas and iii) a carrier gas, wherein and the at least one type of silicon-containing compound in the treated structure is mainly constituted of a compound of the type $SiO_xH_y$, wherein x is in the range of 1 to 4, and y in the range of 0 to 4.

12. A fibrous structure according to claim 11, characterized in that said run-off level has been accomplished by bonding one or more types of polar, silicon-containing compounds, to at least one portion of the surface of the fibrous structure.

13. A fibrous structure according to claim 11, wherein the neither the surface active agent nor the polar, silicon-containing compounds completely cover the surface of the fibrous structure.

14. A fibrous structure according to claim 11, characterized in that said fibrous structure exhibits a predetermined degree of hydrophilicity which is substantially unaffected by wetting of said fibrous structure.

15. A fibrous hydrophobic structure treated to be rendered hydrophilic and exhibiting a run-off level determined by a series of run-off tests, said fibrous structure comprising:

one or more types of polar, silicon-containing compounds bonded to a surface of said fibrous structure via a corona treatment; and an organosilicon based surface active agent or a composition comprising an organosilicon based surface active agent applied to said fibrous structure, wherein, said corona treatment comprises exposing said surface to a corona discharge in the presence of a gaseous mixture comprising at least one type of silicon-containing compound, oxygen or other oxygen-containing gas, and a carrier gas, said at least one type of silicon-containing compound in the treated structure is mainly constituted of a compound of the type $SiO_xH_y$, wherein x is in the range of 1 to 4, and y in the range of 0 to 4, and each run-off test comprises exposing said fibrous structure to a volume of 25 ml of a test solution, said fibrous structure exhibits a run-off level that is zero throughout a series of run-off tests, and the series starts with a first run-off test and ends with a fifth run-off test, and said test solution has a surface tension before the first run-off test which is above $70*10^{-3}$ N/m and a surface tension after the first run-off test which is less than $60*10^{-3}$ N/m.

16. The fibrous hydrophobic structure according to claim 15, wherein said surface active agent is applied to said fibrous structure by a kiss roll technique.

17. The fibrous hydrophobic structure according to claim 15, wherein said composition comprising said surface active agent is applied to said fibrous structure by spraying said composition.

18. The fibrous structure according to claim 15, wherein, said corona treatment further comprises exposing said surface to a corona discharge under air or under an atmosphere comprising a carrier gas and an oxidizing gas, prior to exposing said fibrous structure to a corona discharge in the presence of said gaseous mixture.

19. The fibrous hydrophobic structure according to claim 15, wherein said fibrous structure is polypropylene.

20. The fibrous hydrophobic structure according to claim 1, wherein said fibrous structure is polypropylene.

21. The fibrous hydrophobic structure according to claim 1, wherein said surface active agent is applied to said fibrous structure by a kiss roll technique.

22. The fibrous hydrophobic structure according to claim 1, wherein said composition comprising said surface active agent is applied to said fibrous structure by spraying said composition.

* * * * *